(12) United States Patent
Dou et al.

(10) Patent No.: US 7,676,122 B2
(45) Date of Patent: Mar. 9, 2010

(54) APPARATUS, SYSTEM AND METHOD FOR PARTICLE MANIPULATION USING WAVEGUIDES

(76) Inventors: Jiahua James Dou, 1202-3 Navy Wharf Crt., Toronto, Ontario (CA) M5V 3V1; Luc Charron, 2305 Newscastle Cres., Toronto, Ontario (CA) L5M 4P5; James Stewart Altchison, 14 St. Andrews Garden, Toronto, Ontario (CA) M4W 2E1; Peter Robert Herman, 987 Crosthampton Lane, Mississauga, Ontario (CA) L5H 2X2; Lothar Lilge, 12 Indian Trail, Toronto, Ontario (CA) M8R 1Z7

( * ) Notice: Subject to any disclaimer, the term of this patent is extended or adjusted under 35 U.S.C. 154(b) by 0 days.

(21) Appl. No.: 11/954,189

(22) Filed: Dec. 11, 2007

(65) Prior Publication Data

US 2008/0138010 A1   Jun. 12, 2008

Related U.S. Application Data

(60) Provisional application No. 60/869,490, filed on Dec. 11, 2006.

(51) Int. Cl.
*G02B 6/12* (2006.01)
*C02F 1/02* (2006.01)
*C02F 1/00* (2006.01)

(52) U.S. Cl. .............. 385/14; 210/745; 210/600
(58) Field of Classification Search ......... 385/129–132, 385/14; 210/600, 745
See application file for complete search history.

(56) References Cited

U.S. PATENT DOCUMENTS

| 6,067,859 | A   * | 5/2000  | Kas et al. .............. 73/800    |
| 7,068,874 | B2  * | 6/2006  | Wang et al. ............ 385/16     |
| 2002/0121443 | A1 * | 9/2002  | O'Connell ............ 204/547      |
| 2005/0207940 | A1 * | 9/2005  | Butler et al. .......... 422/73     |
| 2005/0287696 | A1 * | 12/2005 | Dumais et al. ......... 438/69      |
| 2006/0163119 | A1 * | 7/2006  | Hirano et al. ......... 209/210     |
| 2006/0257089 | A1 * | 11/2006 | Mueth et al. .......... 385/125     |
| 2007/0091442 | A1 * | 4/2007  | MacDonald et al. ..... 359/614      |

* cited by examiner

*Primary Examiner*—Charlie Peng

(57) ABSTRACT

A system and method are provided for manipulating particles using waveguides. An optical beam propagated by optical waveguides deflects particles for sorting or subsequent analysis. The present invention is well-suited for the sorting, manipulation and analysis of biological cells. Novel waveguide manufacturing method and materials, as well as monolithic integration and packaging of optofluidic devices are also provided.

18 Claims, 4 Drawing Sheets

APPARATUS, SYSTEM AND METHOD FOR PARTICLE MANIPULATION USING WAVEGUIDES

PRIORITY

This patent application claims priority from U.S. Provisional Application No. 60/869,490, filed on Dec. 11, 2006.

FIELD OF THE INVENTION

The present invention generally relates to a system and method for particle sorting, selecting, manipulation, and analysis. More specifically the present invention relates to integrated optofluidic devices.

BACKGROUND OF THE INVENTION

Particle sorting, selecting, and manipulation apparati have been designed for a number of applications. Depending on the particles, the underlying mechanisms of different sorting devices may offer certain advantages to others. For example, biological particles (such as cells) are one type of particle that may have particular requirements for sorting, selecting, manipulation, and analysis.

Hydrodynamic pressure control, electrokinetics, and radiation pressure are three common approaches used in current particle/cell sorting systems. In particular, laser trapping and guiding by photon pressure is a known technique for sorting particles. A radiation pressure based cell sorting mechanism is generally preferred due to less induced cell stress and disturbance, along with a simple means for integration.

A radiation pressure based cell sorting device was disclosed in U.S. Pat. No. 4,887,721 to Martin et al. This patent describes using photon pressure to propel particles along paths predefined by laser beams. The setup involves a probing laser beam to characterize the optical property of particles and a deflection beam to propel the selected objects. Unfortunately, the system uses free space optics and its components are bulky and difficult to package into an integrated device. As well, the system is only suitable for considerably large objects (greater than 1 mm), and the length scale of the instrument is on the order of millimeters.

U.S. Pat. No. 7,068,874 to Wang et al. also describes a cell sorting device using microfluidic systems molded in PDMS clear plastic. In this approach, a laser beam of Laguerre-Gaussian profile, emanating from Vertical Cavity Surface Emitting Laser (VCSEL) is launched in free space from the top of the device. By moving around the PDMS microfluidic device on a micromanipulation stage, one can effectively manipulate the particles on the plastic chip. This setup, however, relies on sophisticated free space optics for laser beam collimating, shaping and focusing to achieve desired intensity structure in order to produce effective laser tweezing, making it very difficult to integrate to form a complete and self-contained apparatus for cell manipulation purposes.

Various techniques of fabricating waveguides in semiconductor and transparent material have been developed.

For example, U.S. Pat. No. 7,116,878 describes a waveguide structure that consists of a core layer, a cladding layer, and a buffer layer in which optical signals can be confined and manipulated.

As well, U.S. Pat. No. 7,120,325 teaches a 2D optical waveguide that comprises light transmitting and receiving units to enable monolithic integration of optical transmission. These devices, however, are not suitable for biological application and are difficult to interconnect with microfluidic systems.

A UV embossing technique was disclosed in U.S. Pat. No. 6,341,190, in which waveguiding structures can be made onto plastic films or glass, silicon substrates. The process, however, is tedious, and difficult to interconnect with microfluidic networks on a single platform.

In view of the foregoing, what is needed are systems and methods for manipulating particles using waveguides that are simple and effective, and overcome the disadvantages and limitations of current techniques.

SUMMARY OF THE INVENTION

In one aspect of the invention, a system for particle sorting, selecting, manipulating, or analyzing using optical waveguides is provided, comprising a microfluidic particle sorting apparatus, the particle sorting apparatus including: (a) at least one microfluidic main channel for receiving a microfluidic stream of particles; (b) at least one microfluidic transverse channel communicating with the main channel for receiving target particles having defined characteristics from the stream of particles, the transverse channel being disposed generally transverse of the main channel; and (c) at least one optical waveguide disposed adjacent to the at least one transverse channel, and aligned with the transverse channel so as to deliver an optical beam that deflects the target particles into the transverse channel.

In another aspect of the invention, a method of manufacturing an optical waveguide within a substrate for use in connection with a microfluidic particle delivery system for soring, selecting, manipulating or analyzing particles is also provided, the method comprising: (a) etching into the substrate one or more channels for receiving an optical waveguide, the one or more channels being disposed on the substrate such that upon assembly of the substrate with a microfluidic particle delivery system, the microfluidic particle delivery system including: at least one microfluidic main channel for receiving a microfluidic stream of particles; and at least one microfluidic transverse channel communicating with the main channel for receiving target particles having defined characteristics from the stream of particles, the transverse channel being disposed generally transverse of the main channel; wherein said at least one or more channels for receiving the optical waveguide are disposed adjacent to and aligned with the transverse channel upon assembly; (b) injecting a curable compound into the one or more channels for receiving the optical waveguide; and (c) curing the curable compound to form a core for the optical waveguide, the optical waveguide being operable to deflect the target particles into the transverse channel.

In a still other aspect of the invention, a method of sorting, selecting, manipulating, or analyzing target particles from a flow of particles is provided, comprising the steps of: (a) defining one or more characteristics of the target particles; (b) providing a system for sorting, selecting, manipulating, or analyzing the target particles using optical waveguides, the system including a microfluidic particle sorting apparatus, the particle sorting apparatus including: at least one microfluidic main channel for receiving a microfluidic stream of particles; at least one microfluidic transverse channel communicating with the main channel for receiving target particles having defined characteristics from the stream of particles, the transverse channel being disposed generally transverse of the main channel; and at least one optical waveguide disposed adjacent to the at least one transverse channel, and aligned with the transverse channel so as to deliver an optical beam that deflects the target particles into the transverse channel; wherein the system is tunable based on the characteristics; and (c) tuning the system based on the characteristics, and deflecting the target particles to the transverse channel, thereby enabling sorting, selecting, manipulation, or analysis of the target particles.

BRIEF DESCRIPTION OF THE DRAWINGS

A detailed description of the preferred embodiments is provided herein below by way of example only and with reference to the following drawings, in which.

It is to be expressly understood that the description and drawings are only for the purpose of illustration and as an aid to understanding, and are not intended as a definition of the limits of the invention.

DETAILED DESCRIPTION OF THE INVENTION

The present invention is directed a system and method for sorting particles using waveguides. In a further aspect of the invention, it provides an optofluidic system and method for sorting, selecting, manipulating, or analyzing particles, using optical waveguides. In one particular aspect, the optical waveguides are integrated with a microfluidic system, as further particularized below.

In accordance with the present invention, an optofluidic system comprises at least one microfluidic system integrated with one or more optical waveguides. Radiation pressure is provided by an optical beam emanating from the optical waveguides thereby providing force to propel particles along a defined deflection path intersecting a microfluidic main channel (a microfluidic transverse channel) and to deflect particles to the microfluidic transverse channel.

The optical beam, for example, may be a weakly focused, low divergent laser beam having an axial beam intensity gradient effective for transporting the particular particles but ineffective for axially trapping the particles in 3D.

Figure 1:
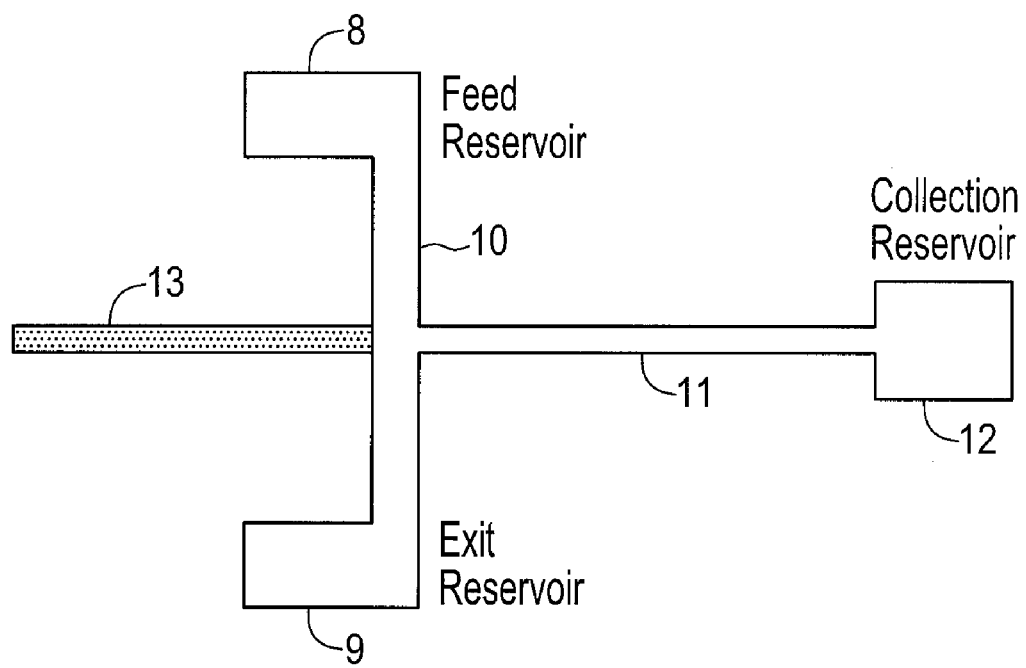
FIG. 1 illustrates a top view of a system in accordance with an embodiment of the present invention.

An embodiment of the particle manipulation system is provided in FIG. 1. The system comprises a microfluidic main channel 10, a feed reservoir 8, an exit reservoir 9, and an optical waveguide 13 disposed in relation to a microfluidic transverse channel 11 so as to be operable to deflect target particles into the microfluidic transverse channel. The transverse channel 11 leads to a collection reservoir 12.

Once deflected into the transverse channel 11, the particles can be collected for future elution and analysis can be carried out, e.g., using optical means, such as forward transmission, or small and large angle scattering measurement and characterization.

In operation, a particle suspension of suitable concentration is injected to feed reservoir 8. The particles are drawn into the main channel 10, size ranging from 10 µm to 100 µm for example, by hydrodynamic pressure or electro-kinetic forces. The propulsion beam, guided by the optical waveguide 13, is weakly divergent at the exiting facet of the waveguide, for example.

"Target" particles, i.e. particles desired to be deflected into the transverse channel 11, may have specific phenotypical characteristics, and are propelled by radiation pressure induced by the optical beam.

In this regard, the system can be "tuned" for the selection of particular particles, either for the analysis of these particular particles or to operate as a means of sorting by separating the particular particles from the stream of particles directed through the main channel 10. For example, the size of the transverse channel 11 may be provided so as to allow particles of a specific size to be deflected into it. In addition, the speed at which the particles are travelling through the main channel 10 can be adjusted thereby affecting which particles are deflected, e.g., the speed is correlated with the optical beam characteristics such that only particles that are below a desired inertia threshold are deflected. Other methods of tuning or optimizing the system are of course possible and would be appreciated by a person of skill in the art.

As suggested, the particular optical beam to be used in conjunction with the system depends on the characteristics of the desired particles to be manipulated. For example, if the particles are biological cells having a diameter between 10 and 100 µm, a continuous near infrared laser source having 50 to 800 mW of power, depending on the coupling efficiency of optical power in the experimental setup, has been found to be effective at deflection. It is preferred that the laser beam have a relatively low divergence. The laser beam can be provided by a laser diode or a vertical-cavity surface-emitting laser, for example.

During operation, biological cells guided by the laser beam delivered using an optical waveguide were observed to be travelling at 22 µm/second in the microfluidic device when the input laser power was about 500 mW, discounting laser-fiber coupling losses. The pre-selected particles are deflected by the propulsion beam into the transverse channel 11 for further analysis. Particles are subsequently collected in exit reservoir 9 or collection reservoir 12. When the deflection beam is turned off, the particles will continue travelling in the main microfluidic channel and arrive in reservoir 9.

The apparatus of the invention is best understood as a particle sorting, selecting, manipulation, and/or analysis apparatus, having the microfluidic main channel and transverse channel, and optical waveguide structure described herein.

Figure 2A:
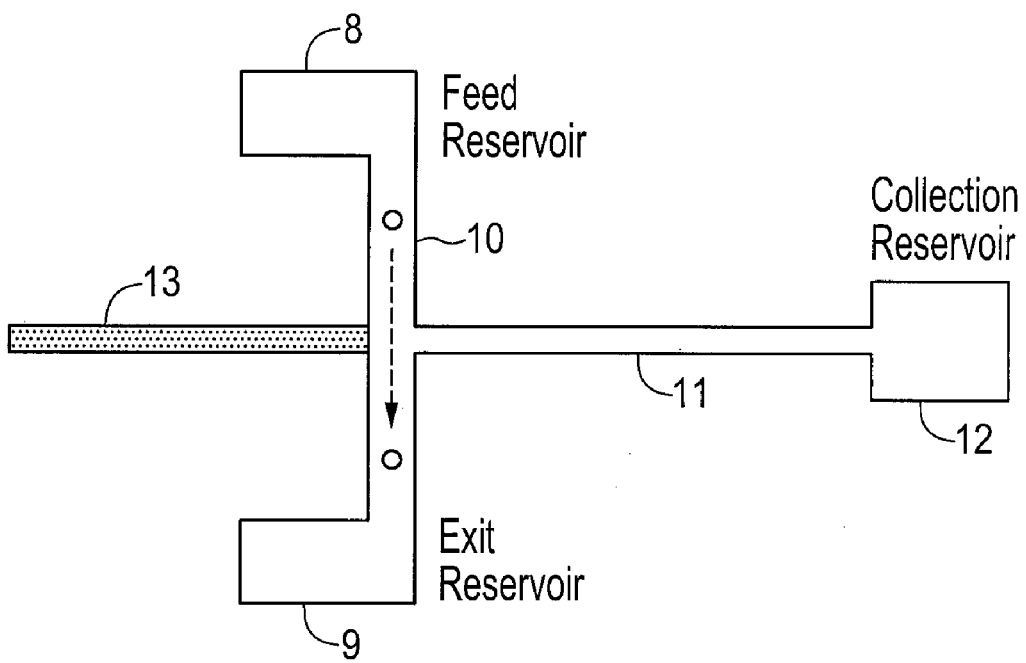
FIG. 2(a) and FIG. 2(b) illustrate a particle moving within a system with a deflection laser off and on, respectively.
Figure 2B:
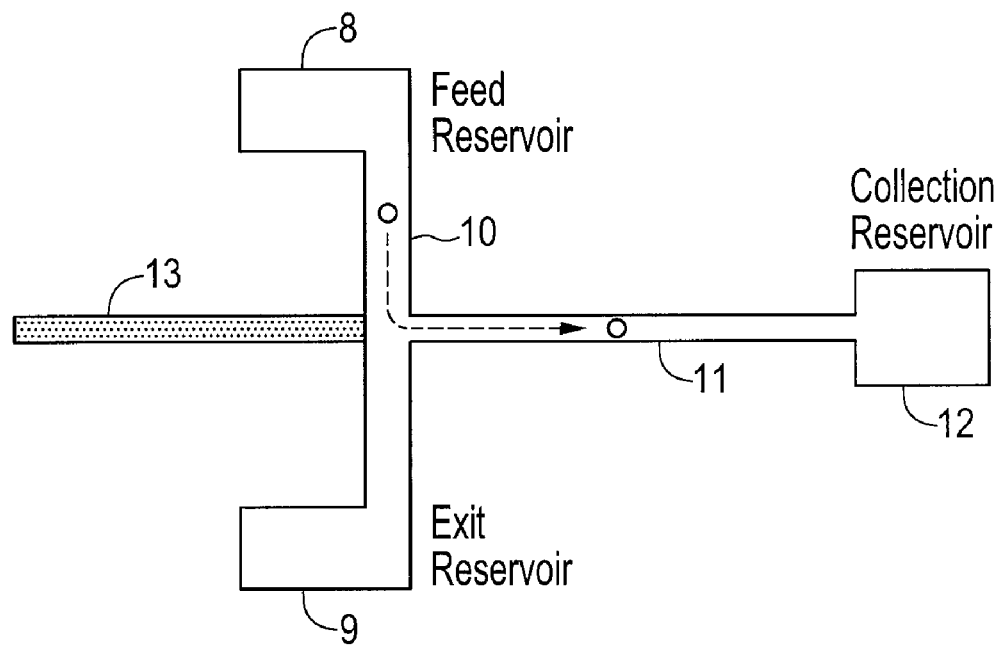

FIG. 2(a) and FIG. 2(b) illustrate the outcomes of the system and apparatus device. In FIG. 2(a), when the laser beam is turned off and the cells will pass through the junction between the main channel 10 and transverse channel 11 as illustrated. In FIG. 2(b), when the laser beam is launched into the waveguide 13, the cells travelling in the main channel 10 will be deflected into the transverse channel 11.

Figure 3:
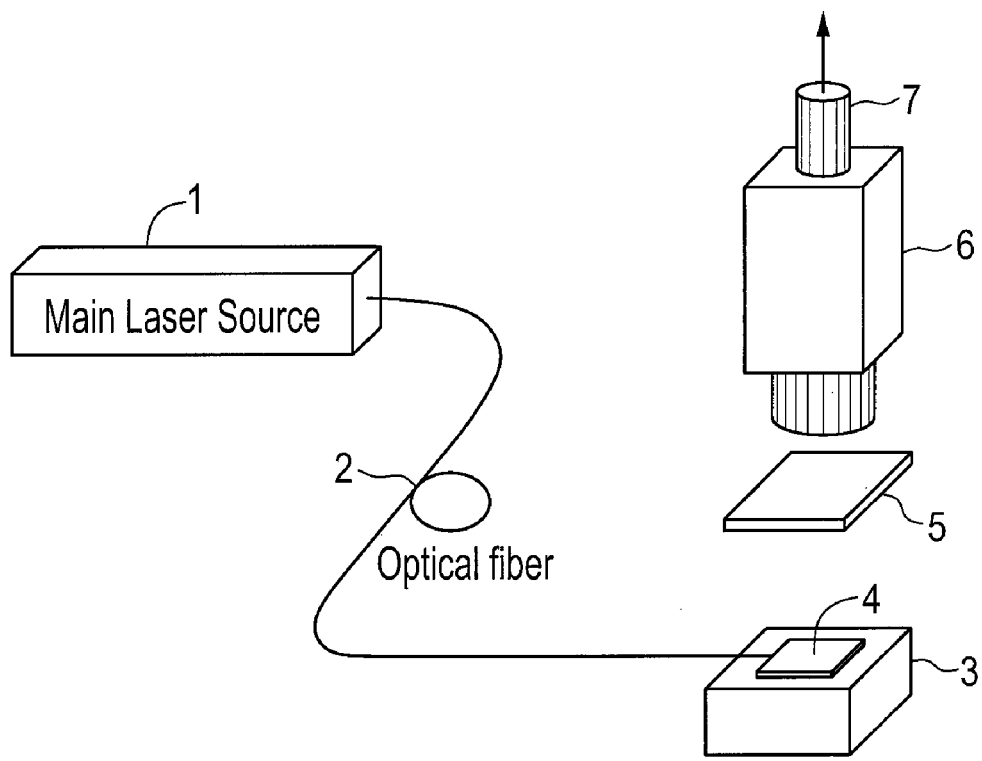
FIG. 3 illustrates a system in accordance with an embodiment of the present invention.

One embodiment of a system is shown schematically in FIG. 3. The system as described above is implemented as a lab-on-a-chip microfluidic system 4. The microfluidic system 4 is placed on a micromanipulation stage 3. An imaging system 7, preferably a CCD camera, measures the light scattering and transmission intensity, fluorescence, etc. A video signal output from camera 7 can also be used directly to analyze particle characteristics and behaviours. The setup employs fiber-optic delivery system to launch laser light into the microfluidic system 4. A laser diode source 1, with emission wavelength ranging from 0.140 µm to 2.3 µm, is connected to a link of optical fiber 2, which is pigtailed to the microfluidic system 4 on the other end.

The laser that provides the propulsion force is launched into the waveguide via the optical fiber 2. An observation device 6, which may be an inverted microscope (Model Axiovert200M™, Carl Zeiss, Germany), may be placed above or under the device. Observations and measurement on the microfluidic system 4 may be sent through a video system. A long-pass filter 5 may be placed before the microscope 6 to block the light scattered from the laser beam.

Figure 4:
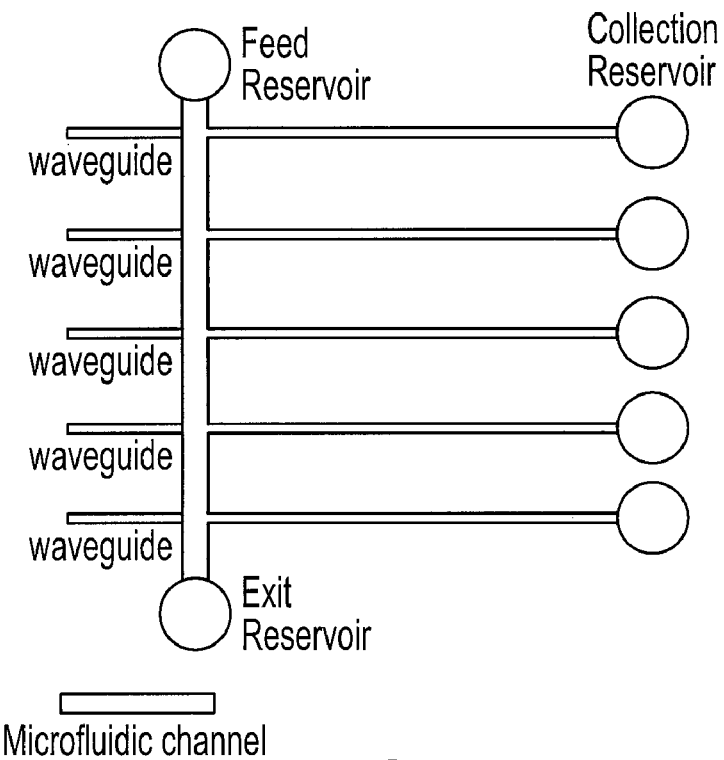
FIG. 4 illustrates a top view of a manipulation system in accordance with an embodiment of the present invention featuring a plurality of waveguides operating in parallel.

The system of the present invention is designed such that future integration and scaling can be easily accomplished, improving the device throughput by parallel processing the same on-chip analysis. For example, a parallel processing system with significant improvement of throughput can be developed by introducing a series of waveguides and microfluidic channels aligned as shown in the FIG. 4. Although FIG. 4 only depicts a series of 6 waveguides and microfluidic channel intersections, the number of channel-waveguide pairs can be arbitrary.

Figure 5:
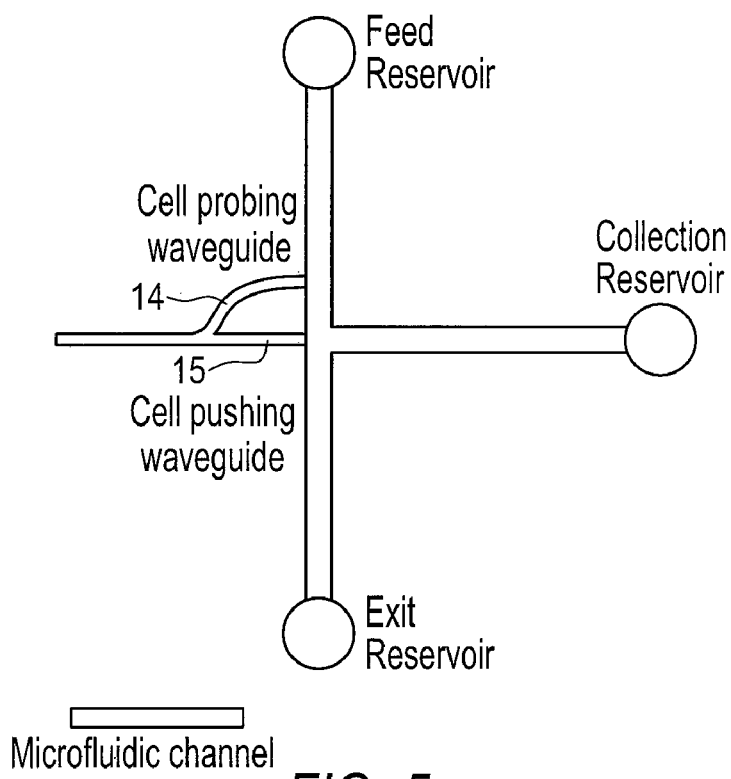
FIG. 5 illustrates a top view of a manipulation system in accordance with an embodiment of the present invention including fluorescence activated sorting capability.
Figure 6:
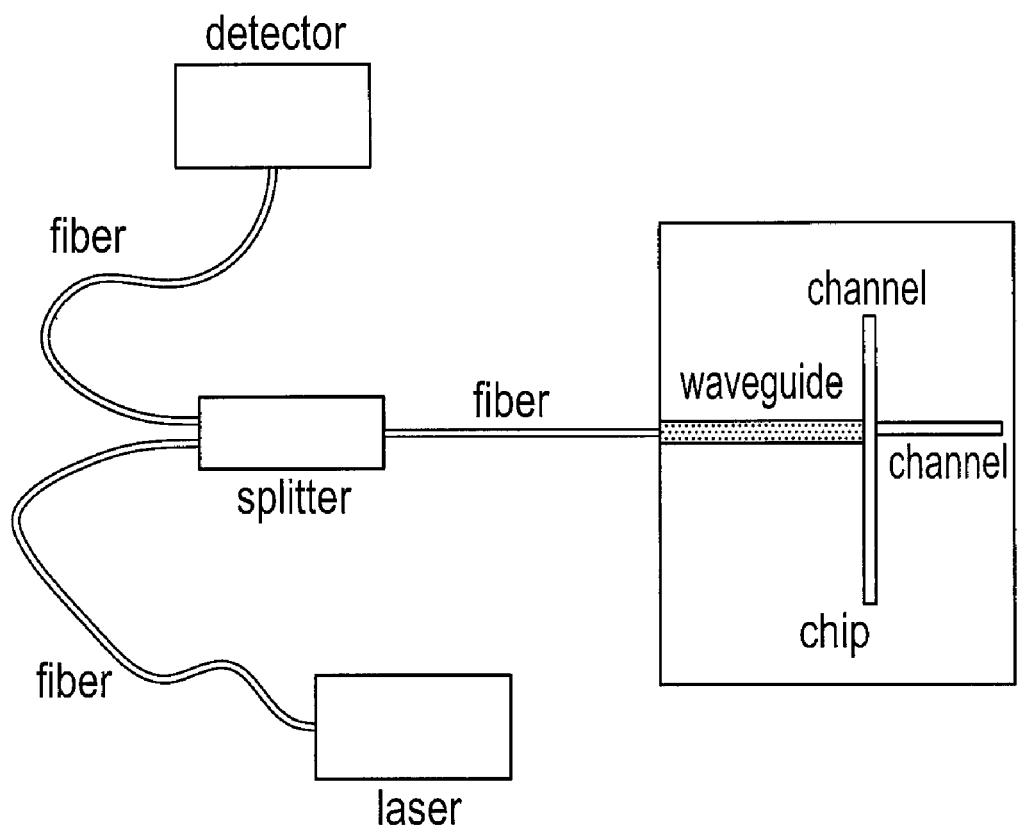
FIG. 6 illustrates an experimental setup in which an optical power splitter is used to allow optical launching and detection using one integrated waveguide.

Another possible modification to the system is illustrated in FIG. 5. In this case, an additional cell-probing waveguide 14 attached to a detector can be introduced in the waveguide-microfluidics intersection. This waveguide is used to probe the particles to determine its physical properties and information acquired can be collected using the same optical circuit. Acquired information can be recorded by a detection device such as an avalanche photodiode, a CCD camera, or via any other suitable optical detection means. The optional probing waveguide could also be the same as the pushing waveguide 15, as shown in FIG. 6. An optical power splitter could be inserted to transmit launching laser power from an optical source such as a laser as well as collecting reflected optical signals via the detector.

In a further aspect, the present invention provides a manufacturing method for producing an optical waveguide using a novel micro-molding technique. The method comprises the following general steps: (i) a channel is etched into a substrate using a microfabrication means; (ii) a curable epoxy is injected into the channel; and (iii) the epoxy is cured to form the optically guiding core of a surface optical waveguide. This method of manufacturing an optical waveguide allows the implementation of optical circuits on the surface of a substrate for facile interception with microfluidic channels, whether the substrate is a polymer as described herein or other suitable material, enabling exceptional integration architectures for forming interconnected surface microfluidic and optical waveguide systems that complete the optofluidic device.

Figure 7:
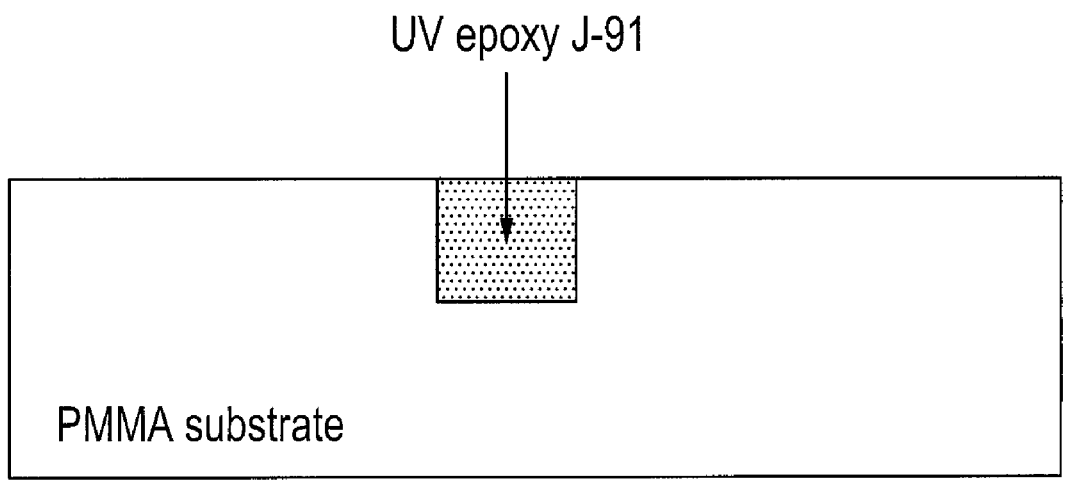
FIG. 7 illustrates a cross-sectional view of an optical waveguide.

For example, a cross-sectional view of a surface optical waveguide is provided in FIG. 7 wherein the substrate is fabricated in polymethyl methacrylate (PMMA). In one embodiment of the method, the fabrication technique consists of first etching a microscopic channel in the PMMA substrate. A curable epoxy is injected into the channel by capillary forces. Upon curing, the cross-linking of the epoxy forms the core of the optical waveguide.

It should be understood that although PMMA and a curable epoxy are described as suitable materials for the substrate and core, the present invention is not limited to these materials for the waveguide. In fact, any biocompatible material could be used for the substrate and any transparent material could be used for the core of the waveguide. However, it has been found that this epoxy material is particularly well-suited for use with a PMMA substrate because of the refractive index difference (approximately 0.04) and low viscosity.

It should be understood that the system of the present invention could be easily and advantageously implemented as a hand-held chip in a PDA-style device, thus offering a small, portable and integrated device ideal for field applications.

As stated above, the manipulation of microscopic objects using radiation pressure offers many advantages, including the following:
1. Radiation pressure induces less stress or damage to the particles, which is critical in biological applications wherein the particles are cells.
2. The use of radiation pressure based devices for cellular manipulation eliminates the tedious pneumatic control valves, pipes and tubes, which generally makes the devices easier to package.
3. Radiation pressure techniques allow for the utilization of existing on-chip optical systems for more complicated optical diagnostics for cellular analysis and characterization.

The present invention is well-suited for biological cell sorting, manipulation and analysis. In particular, this technology is well-suited for point-of-care diagnosis and prognosis of blood disorder diseases such leukemia and lymphoma. In addition, it is useful in monitoring cancer patients' blood quality during chemo- and radiotherapy to aid cancer treatment.

However, the technology also has a wide range application beyond medical purposes, such as general chemical testing, environmental monitoring, agriculture and animal welfare (e.g., testing horse blood), and food safety inspection (e.g., virus detection).

It will be appreciated by those skilled in the art that other variations of the preferred embodiment may also be practiced without departing from the scope of the invention.

What is claimed is:

1. A system for particle sorting, selecting, manipulating, or analyzing using optical waveguides comprising:
   (a) a microfluidic particle sorting, selecting, manipulating, or analyzing apparatus, the apparatus including:
      i. at least one microfluidic main channel for receiving a microfluidic stream of particles;
      ii. at least one microfluidic transverse channel communicating with the main channel for receiving target particles having defined characteristics from the stream of particles, the transverse channel being disposed generally transverse of the main channel; and
      iii. at least one optical waveguide disposed adjacent to the at least one transverse channel, and aligned with the transverse channel so as to deliver an optical beam that deflects the target particles into the transverse channel; and
   (b) a means of tuning the system based on the characteristics, and deflecting the target particles to the transverse channel, thereby enabling sorting, selecting, manipulation, or analysis of the target particles, the system being tunable to deflect target particles based on specific characteristics and the system enabling (a) adjustment of the speed at which the particle suspension travels through the apparatus, and (b) correlating characteristics of the optical beam to the speed, so as to deflect only target particles below a desired inertia threshold.

2. The system of claim 1 including an optical source, the optical source being connected to the optical waveguide.

3. The system of claim 1 wherein the apparatus consists of a substrate including a microfabricated optical circuit on the surface of the substrate that provides the at least one optical waveguide.

4. The system of claim 1 wherein the main channel has two ends, a first end connected to a feed reservoir operable to receive a particle suspension, and a second end connected to an exit reservoir.

5. The system of claim 1 wherein the transverse channel has two ends, a first end connected to and communicating with the main channel and a second end connected to a collection reservoir.

6. The system of claim 4 wherein the particle suspension migrates from the feed reservoir along the main channels to the exit reservoir.

7. The system of claim 6 wherein the particle suspension migrates by way of hydrodynamic pressure.

8. The system of claim 6 wherein the particle suspension migrates by way of electro-kinetic forces.

9. The system of claim 6 wherein the particle suspension is in the size range of 10 μm to 100 μm.

10. The system of claim 7 wherein the particle suspension migrating in the main channel may be deflected into the transverse channel by radiation pressure induced by an optical beam delivered by the optical waveguide.

11. The system of claim 1 wherein the system enables the optical beam to be selected or varied so as to deflect target particles within the particle suspension.

12. The system of claim 1 wherein the optical beam consists of a continuous near infrared laser source having 50 to 800 mW of power wherein the target particles of the particle suspension may be biological cells having a diameter between 10 μm to 100 μm.

13. The system of claim 1 wherein the diameter of the transverse channels is sized to receive through deflection target particles having a specific size within the particle suspension.

14. The system of claim 1 wherein the system further comprises a detector disposed adjacent to the optical waveguide.

15. The system of claim 14 wherein the detector is operable to receive reflected optical signals from particles within the particle suspension and determine physical properties of said particles.

16. The system of claim 14 wherein an optical splitter is connectable to both the optical source and the detector.

17. A method of sorting, selecting, manipulating, or analyzing target particles from a flow of particles comprising the steps of:
(a) defining one or more characteristics of the target particles;
(b) providing a system for sorting, selecting, manipulating, or analyzing the target particles using optical waveguides, the system including a microfluidic particle sorting apparatus, the particle sorting apparatus including:
  i. at least one microfluidic main channel for receiving a microfluidic stream of particles;
  ii. at least one microfluidic transverse channel communicating with the main channel for receiving target particles having defined characteristics from the stream of particles, the transverse channel being disposed generally transverse of the main channel; and
  iii. at least one optical waveguide disposed adjacent to the at least one transverse channel, and aligned with the transverse channel so as to deliver an optical beam that deflects the target particles into the transverse channel;
  wherein the system is tunable based on the characteristics; and
(c) tuning the system based on the characteristics, and deflecting the target particles to the transverse channel, thereby enabling sorting, selecting, manipulation, or analysis of the target particles and enabling (a) adjustment of the speed at which the particle suspension travels through the apparatus, and (b) correlating characteristics of the optical beam to the speed, so as to deflect only target particles below a desired inertia threshold.

18. A microfluidic particle sorting, selecting, manipulating, or analyzing apparatus comprising:
(a) at least one microfluidic main channel for receiving a microfluidic stream of particles;
(b) at least one microfluidic transverse channel communicating with the main channel for receiving target particles having defined characteristics from the stream of particles, the transverse channel being disposed generally transverse of the main channel; and
(c) at least one optical waveguide provided on a substrate embedded in the particle sorting apparatus, the optical waveguide being provided such that it is adjacent to the at least one transverse channel, and aligned with the transverse channel so as to deliver an optical beam that deflects the target particles into the transverse channel, thereby enabling sorting, selecting, manipulating, or analyzing of the target particles particles and enabling (a) adjustment of the speed at which the particle suspension travels through the apparatus, and (b) correlating characteristics of the optical beam to the speed, so as to deflect only target particles below a desired inertia threshold.

* * * * *